United States Patent [19]
Eggers et al.

[11] Patent Number: 5,888,198
[45] Date of Patent: *Mar. 30, 1999

[54] ELECTROSURGICAL SYSTEM FOR RESECTION AND ABLATION OF TISSUE IN ELECTRICALLY CONDUCTIVE FLUIDS

[75] Inventors: Philip E. Eggers, Dublin, Ohio; Hira V. Thapliyal, Mountain View, Calif.

[73] Assignee: ArthroCare Corporation, Sunnyvale, Calif.

[*] Notice: The term of this patent shall not extend beyond the expiration date of Pat. No. 5,366,443.

[21] Appl. No.: 766,382

[22] Filed: Dec. 5, 1996

Related U.S. Application Data

[60] Division of Ser. No. 446,767, Jun. 2, 1995, Pat. No. 5,697,909, which is a continuation-in-part of Ser. No. 59,681, May 10, 1993, abandoned, which is a continuation-in-part of Ser. No. 958,977, Oct. 9, 1992, Pat. No. 5,366,443, which is a continuation-in-part of Ser. No. 817,575, Jan. 7, 1992, abandoned.

[51] Int. Cl.⁶ ........................................................ A61B 1/00
[52] U.S. Cl. ............................................................. 604/114
[58] Field of Search ................................. 604/20–22, 113, 604/114, 27, 29, 30, 32, 35, 38; 606/28, 31, 41, 194

[56] References Cited

U.S. PATENT DOCUMENTS

| | | |
|---|---|---|
| 2,050,904 | 8/1936 | Trice . |
| 3,812,858 | 5/1974 | Oringer .................................... 604/22 |
| 4,033,351 | 7/1977 | Hetzel ....................................... 606/48 |
| 4,040,426 | 8/1977 | Morrison, Jr. ........................... 128/303 |
| 4,043,342 | 8/1977 | Morrison, Jr. ............................. 606/48 |
| 4,116,198 | 9/1978 | Roos ......................................... 128/303 |
| 4,184,492 | 1/1980 | Meinke et al. ........................... 128/303 |
| 4,202,337 | 5/1980 | Hren et al. ................................ 128/303 |
| 4,228,800 | 10/1980 | Degler, Jr. et al. ..................... 128/303 |
| 4,240,441 | 12/1980 | Khalil ...................................... 128/692 |

(List continued on next page.)

FOREIGN PATENT DOCUMENTS

| | | |
|---|---|---|
| 515 867 | 12/1992 | European Pat. Off. ........ A61B 17/36 |
| 0 597 463 | 5/1994 | European Pat. Off. ......... A61N 5/04 |
| 0 703 461 A2 | 3/1996 | European Pat. Off. ........ G01R 27/02 |
| 0 740 926 | 11/1996 | European Pat. Off. ........ A61B 17/39 |
| 0 740 926 A2 | 11/1996 | European Pat. Off. ........ A61B 17/39 |
| WO 90/07303 | 7/1990 | WIPO ........................... A61B 17/39 |
| WO 91/13650 | 9/1991 | WIPO .............................. A61N 5/04 |
| WO 92/21278 | 12/1992 | WIPO .............................. A61B 5/04 |
| WO 93/13816 | 7/1993 | WIPO ............................ A61B 17/36 |
| Wo 93/20747 | 10/1993 | WIPO ............................. A61N 1/06 |
| WO 94/04220 | 3/1994 | WIPO ............................. A61N 1/06 |
| 94/08654 | 4/1994 | WIPO ........................... A61M 37/00 |
| WO 94/14383 | 7/1994 | WIPO ........................... A61B 17/36 |
| WO 94/26228 | 11/1994 | WIPO ........................... A61G 17/36 |
| WO 95/34259 | 12/1995 | WIPO ............................. A61F 5/48 |
| 97/00646 | 1/1997 | WIPO ........................... A61B 17/39 |
| 97/00647 | 1/1997 | WIPO ........................... A61B 17/39 |

OTHER PUBLICATIONS

P. C. Nardella (1989) *SPIE* 1068:42–49 Radio Frequency Energy and Impedance Feedback.

(List continued on next page.)

*Primary Examiner*—John D. Yasko
*Assistant Examiner*—Manuel Mendez
*Attorney, Agent, or Firm*—John T. Raffle

[57] ABSTRACT

An electrosurgical system comprises an electrosurgical probe and an electrosurgical power supply for ablation and resection of soft tissue in the presence of electrically conductive fluids, such as isotonic saline. In one embodiment, the probe includes a shaft having an electrode array with a plurality of electrically isolated electrode terminals and a return electrode spaced proximally from the electrode array. The power supply includes a plurality of current limiting elements for limiting current based on impedance between the electrode terminals and the return electrode. By applying high frequency voltage to the electrode array, target tissue may be cut or ablated while heat dissipation through low impedance paths, such as saline, is minimized. The power supply has an operating frequency less than 400 kHz, usually about 100 kHz, for limiting current penetration into the tissue.

32 Claims, 10 Drawing Sheets

U.S. PATENT DOCUMENTS

| | | | |
|---|---|---|---|
| 4,248,231 | 2/1981 | Herczog et al. | 128/303 |
| 4,326,529 | 4/1982 | Doss | 128/303.1 |
| 4,381,007 | 4/1983 | Doss | 128/303.1 |
| 4,476,862 | 10/1984 | Pao | 128/303.17 |
| 4,532,924 | 8/1985 | Auth et al. | 128/303 |
| 4,548,207 | 10/1985 | Reimels | 128/303 |
| 4,567,890 | 2/1986 | Ohta et al. | 128/303.13 |
| 4,593,691 | 5/1986 | Lindstrom et al. | 128/303.14 |
| 4,658,817 | 4/1987 | Hardy | 128/303 |
| 4,674,499 | 6/1987 | Pao | 128/303 |
| 4,682,596 | 7/1987 | Bales et al. | 128/303 |
| 4,706,667 | 11/1987 | Roos | 128/303 |
| 4,709,698 | 12/1987 | Johnston et al. | 128/303 |
| 4,736,743 | 4/1988 | Daikuzono | 128/303.1 |
| 4,737,678 | 4/1988 | Hasegawa | 313/36 |
| 4,762,128 | 8/1988 | Rosenbluth | 128/343 |
| 4,765,331 | 8/1988 | Petruzzi et al. | 128/303 |
| 4,785,806 | 11/1988 | Deckelbaum | 128/303.1 |
| 4,813,429 | 3/1989 | Eshel et al. | 128/736 |
| 4,823,791 | 4/1989 | D'Amelio et al. | 123/303 |
| 4,827,911 | 5/1989 | Broadwin et al. | 604/22 |
| 4,931,047 | 6/1990 | Broadwin et al. | 604/22 |
| 4,936,301 | 6/1990 | Rexroth et al. | 606/45 |
| 4,943,290 | 7/1990 | Rexroth et al. | 606/45 |
| 4,955,377 | 9/1990 | Lennox et al. | 128/401 |
| 4,967,765 | 11/1990 | Turner et al. | 128/785 |
| 4,968,314 | 11/1990 | Michaels | 606/7 |
| 4,976,711 | 12/1990 | Parins et al. | 606/48 |
| 4,979,948 | 12/1990 | Geddes et al. | 606/33 |
| 4,998,933 | 3/1991 | Eggers et al. | 606/41 |
| 5,007,437 | 4/1991 | Sterzer | 428/786 |
| 5,009,656 | 4/1991 | Reimels | 606/48 |
| 5,037,421 | 8/1991 | Boutacoff et al. | 606/15 |
| 5,057,105 | 10/1991 | Malone et al. | 606/28 |
| 5,061,266 | 10/1991 | Hakky | 606/15 |
| 5,078,717 | 1/1992 | Parins et al. | 606/48 |
| 5,080,660 | 1/1992 | Buelna | 606/48 |
| 5,083,565 | 1/1992 | Parins | 128/642 |
| 5,098,431 | 3/1992 | Rydell | 606/48 |
| 5,102,410 | 4/1992 | Dressel | 606/15 |
| 5,108,391 | 4/1992 | Flachenecker et al. | 606/38 |
| 5,112,330 | 5/1992 | Nishigaki et al. | 606/46 |
| 5,122,138 | 6/1992 | Manwaring | 606/46 |
| 5,125,928 | 6/1992 | Parins et al. | 606/48 |
| 5,147,354 | 9/1992 | Boutacoff et al. | 606/15 |
| 5,151,098 | 9/1992 | Loertscher | 606/16 |
| 5,178,620 | 1/1993 | Eggers et al. | 606/41 |
| 5,190,517 | 3/1993 | Zieve et al. | 604/22 |
| 5,195,959 | 3/1993 | Smith | 604/34 |
| 5,197,963 | 3/1993 | Parins | 606/46 |
| 5,217,455 | 6/1993 | Tan | 606/9 |
| 5,217,457 | 6/1993 | Delahuerga et al. | 606/42 |
| 5,249,585 | 10/1993 | Turner et al. | 607/99 |
| 5,261,410 | 11/1993 | Alfano et al. | 128/664 |
| 5,267,994 | 12/1993 | Gentelia et al. | 606/15 |
| 5,267,997 | 12/1993 | Farin et al. | 606/38 |
| 5,273,524 | 12/1993 | Fox et al. | 604/21 |
| 5,277,201 | 1/1994 | Stern | 607/98 |
| 5,281,216 | 1/1994 | Klicek | 606/42 |
| 5,281,218 | 1/1994 | Imran | 606/41 |
| 5,282,797 | 2/1994 | Chess | 606/9 |
| 5,290,273 | 3/1994 | Tan | 606/9 |
| 5,290,282 | 3/1994 | Casscells | 607/29 |
| 5,300,069 | 4/1994 | Hunsberger et al. | 606/37 |
| 5,300,099 | 4/1994 | Rudie | 607/101 |
| 5,301,687 | 4/1994 | Wong et al. | 607/116 |
| 5,304,170 | 4/1994 | Green | 606/9 |
| 5,312,395 | 5/1994 | Tan et al. | 606/9 |
| 5,312,400 | 5/1994 | Bales et al. | 606/41 |
| 5,314,406 | 5/1994 | Arias et al. | 604/21 |
| 5,322,507 | 6/1994 | Costello et al. | 128/4 |
| 5,324,254 | 6/1994 | Phillips | 604/21 |
| 5,326,343 | 7/1994 | Rudie et al. | 607/101 |
| 5,330,518 | 7/1994 | Neilson et al. | 607/101 |
| 5,334,140 | 8/1994 | Phillips | 604/35 |
| 5,334,183 | 8/1994 | Wuchinich | 606/46 |
| 5,336,217 | 8/1994 | Buys et al. | 606/9 |
| 5,336,220 | 8/1994 | Ryan et al. | 604/22 |
| 5,342,357 | 8/1994 | Nardella | 606/40 |
| 5,366,443 | 11/1994 | Eggers et al. | 604/114 |
| 5,370,642 | 12/1994 | Keller | 606/9 |
| 5,370,675 | 12/1994 | Edwards et al. | 607/101 |
| 5,380,277 | 1/1995 | Phillips | 604/33 |
| 5,380,316 | 1/1995 | Aita et al. | 606/7 |
| 5,383,876 | 1/1995 | Nardella | 606/49 |
| 5,383,917 | 1/1995 | Desai et al. | 607/702 |
| 5,389,096 | 2/1995 | Aita et al. | 606/15 |
| 5,395,312 | 3/1995 | Desai | 604/22 |
| 5,417,687 | 5/1995 | Nardella et al. | 606/32 |
| 5,419,767 | 5/1995 | Eggers et al. | 604/114 |
| 5,423,803 | 6/1995 | Tankovich | 606/9 |
| 5,423,882 | 6/1995 | Jackman et al. | 607/122 |
| 5,445,634 | 8/1995 | Keller | 606/9 |
| 5,454,809 | 10/1995 | Janssen | 606/41 |
| 5,569,242 | 10/1996 | Lax et al. | 606/42 |
| 5,681,282 | 10/1997 | Eggers et al. | 604/114 |
| 5,697,281 | 12/1997 | Eggers et al. | 604/114 |
| 5,697,536 | 12/1997 | Eggers et al. | 604/114 |
| 5,697,882 | 12/1997 | Eggers et al. | 604/114 |
| 5,697,909 | 12/1997 | Eggers et al. | 604/114 |
| 5,766,153 | 6/1998 | Eggers et al. | 604/114 |
| 5,810,764 | 9/1998 | Eggers et al. | 604/23 |

OTHER PUBLICATIONS

Rand et al. (1985) *J. Arthro. Surg.* 1:242–246 Effect of Electrocautery on Fresh Human Articular Cartilage.

Rand, J. A. et al. "Effect of Electrocautery on Fresh Human Articular Cartilage," (1985) Arthroscopy, The Journal of Arthrocopic and Related Surgery, pp. 242–246.

Buchelt, M. et al. "Excimer Laser Ablation of Fibrocartilage: An In Vitro and In Vivo Study," (1991) Lasers in Surgery and Medicine 11:271–279.

Costello, A. J. et al. "Nd:YAG Laser Ablation of the Prostate as a Treatment of Benign Prostatic Hypertrophy," (1992) Lasers in Surger and Medicine 12:121–124.

V.E. Elsasser et al. *Acta Medicotechnica* vol. 24, No. 4, pp. 129–134 (1976).

E.V. Kramolowsky et al. *J. of Urology* vol 143, pp. 275–277 (1990).

J.W. Ramsey et al. *Urological Research* vol. 13, pp. 99–102 (1985).

R. Tucker et al., Abstract P14–11, p. 248, "A Bipolar Electrosurgical Turp Loop".

R. Tucker et al. *J. of Urology* vol. 141, pp. 662–665, (1989).

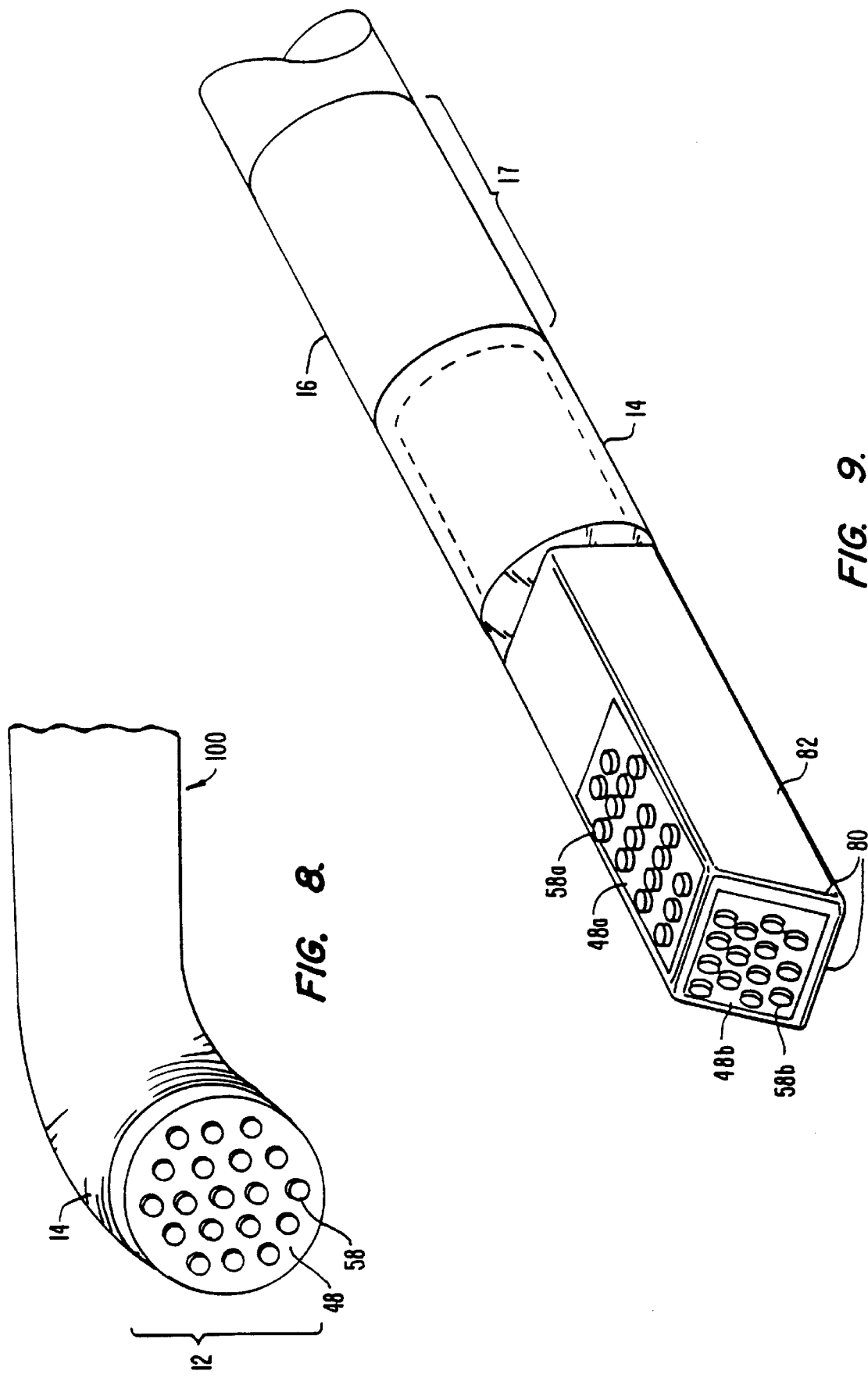

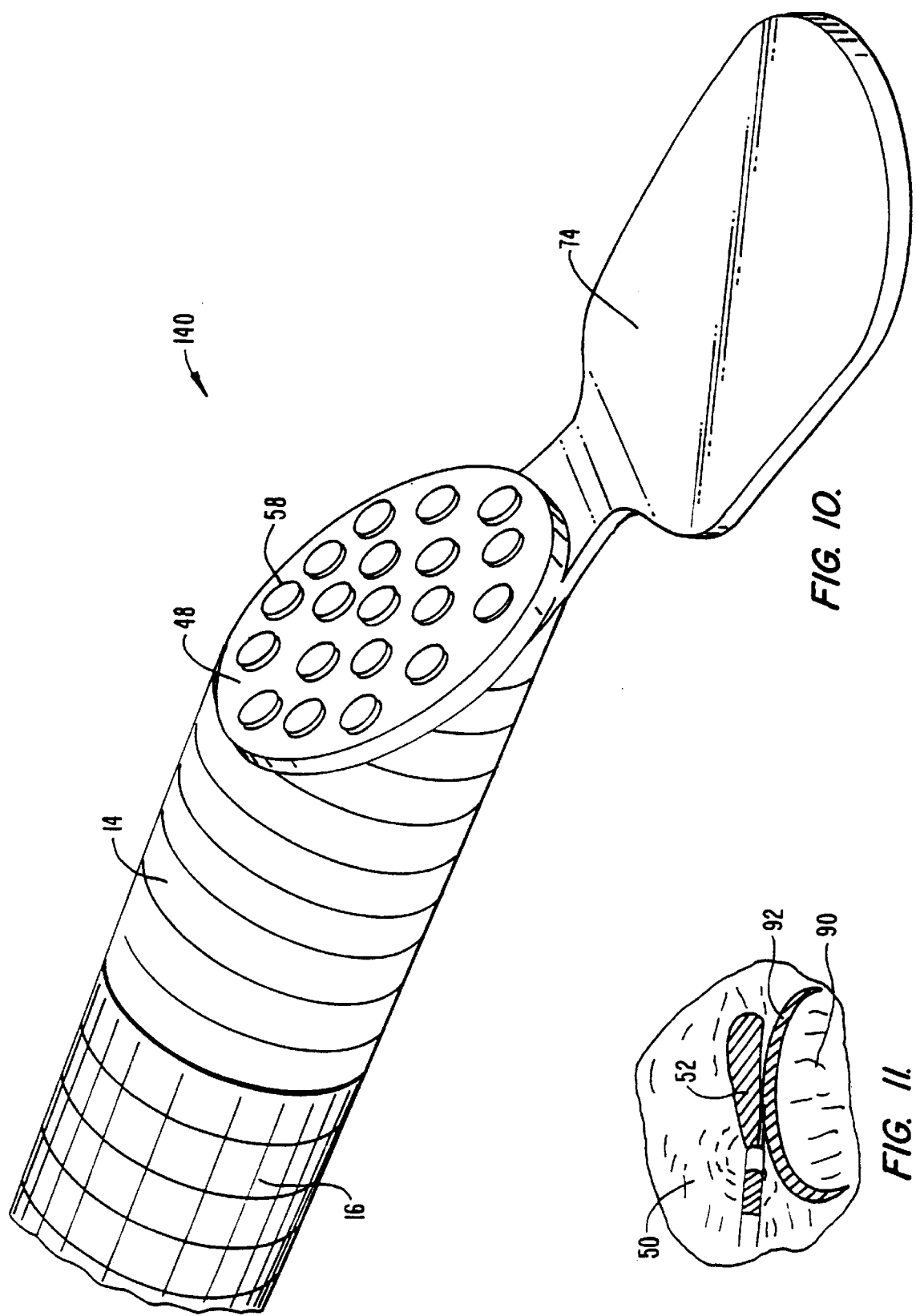

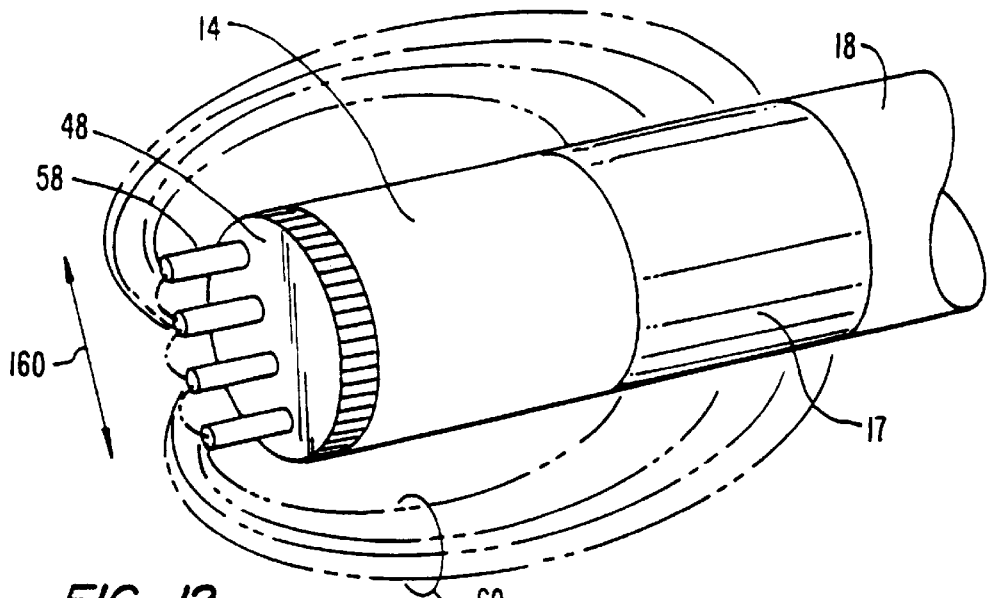
FIG. 12.
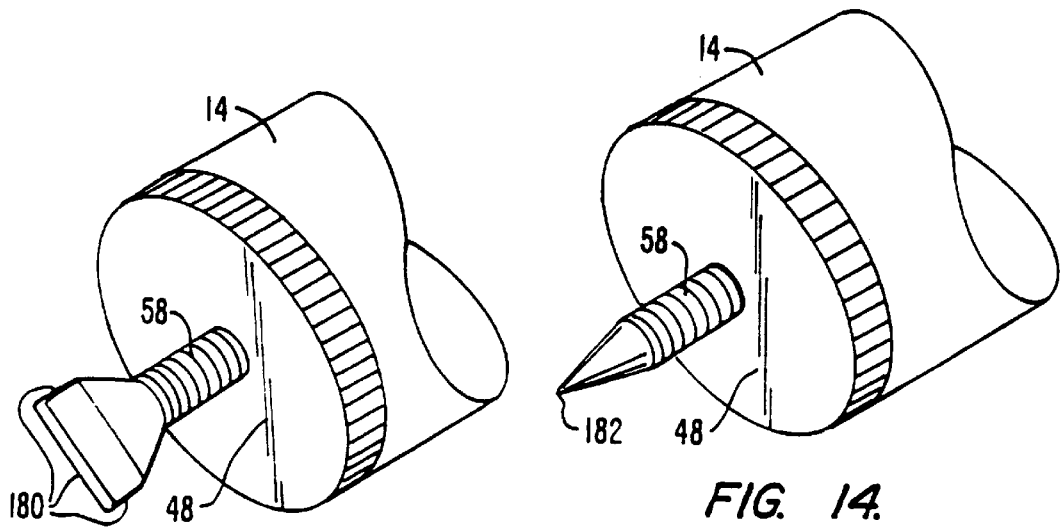
FIG. 13.
FIG. 14.
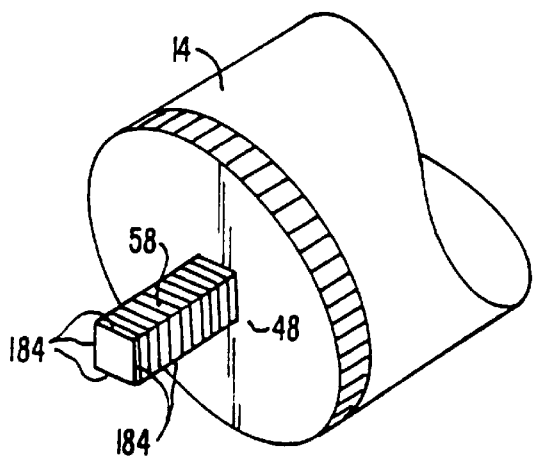
FIG. 15.

ELECTROSURGICAL SYSTEM FOR RESECTION AND ABLATION OF TISSUE IN ELECTRICALLY CONDUCTIVE FLUIDS

This is a division of application Ser. No. 08/446,767 filed Jun. 2, 1995, now U.S. Pat. No. 5,697,909, which is CIP of Ser. No. 08/059,681, filed May 10, 1993, now abandoned; which is a CIP of Ser. No. 08/958,977, filed Oct. 9, 1992, now U.S. Pat. No. 5,366,443; which is a CIP of Ser. No. 08/817,575, filed Jan. 7, 1992, now abandoned.

BACKGROUND OF THE INVENTION

1. Field of the Invention

The present invention relates generally to the field of electrosurgery and, more particularly, to surgical devices and methods which employ very high frequency electrodes comprising an array of individual, isolated electrode terminals.

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on external grounding of the patient, where the surgical device defines only a single electrode pole. Bipolar devices comprise both electrodes for the application of current between their surfaces.

Electrosurgical procedures and techniques are particularly advantageous since they generally reduce patient bleeding and trauma associated with cutting operations. Additionally, electrosurgical ablation procedures, where tissue surfaces and volume may be reshaped, cannot be duplicated through other treatment modalities.

The use of electrosurgical procedures in electrically conductive environments, however, can be problematic. For example, many arthroscopic procedures require flushing of the region to be treated with isotonic saline (also referred to as normal saline), both to maintain an isotonic environment and to keep the field of viewing clear. The presence of saline, which is a highly conductive electrolyte, can cause shorting of the electrosurgical electrode in both monopolar and bipolar modes. Such shorting causes unnecessary heating in the treatment environment and can further cause non-specific tissue destruction.

Present electrosurgical techniques used for tissue ablation also suffer from an inability to control the depth of necrosis in the tissue being treated. Most electrosurgical devices rely on creation of an electric arc between the treating electrode and the tissue being cut or ablated to cause the desired localized heating. Such arcs, however, often create very high temperatures causing a depth of necrosis greater than 500 $\mu$m, frequently greater than 800 $\mu$m, and sometimes as great as 1700 $\mu$m. The inability to control such depth of necrosis is a significant disadvantage in using electrosurgical techniques for tissue ablation, particularly in arthroscopic procedures for ablating and/or reshaping fibrocartilage, articular cartilage, meniscal tissue, and the like.

In an effort to overcome at least some of these limitations of electrosurgery, laser apparatus have been developed for use in arthroscopic and other procedures. Lasers do not suffer from electrical shorting in conductive environments, and certain types of lasers allow for very controlled cutting with limited depth of necrosis. Despite these advantages, laser devices suffer from their own set of deficiencies. In the first place, laser equipment can be very expensive because of the costs associated with the laser light sources. Moreover, those lasers which permit acceptable depths of necrosis (such as excimer lasers, erbium:YAG lasers, and the like) provide a very low volumetric ablation rate, which is a particular disadvantage in cutting and ablation of fibrocartilage, articular cartilage, and meniscal tissue. The holmium:YAG and Nd:YAG lasers provide much higher volumetric ablation rates, but are much less able to control depth of necrosis than are the slower laser devices. The $CO_2$ lasers provide high rate of ablation and low depth of tissue necrosis, but cannot operate in a liquid-filled cavity.

For these reasons, it would be desirable to provide improved apparatus and methods for efficiently cutting and ablating tissue, particularly fibrocartilage, articular cartilage, meniscal tissue, and the like in arthroscopic and other procedures. Such apparatus and methods should be able to selectively cut and ablate tissue and other body structures in electrically conductive environments, particularly regions which are filled with blood, irrigated with saline, or the like. Such apparatus and methods should be able to perform cutting and ablation of tissues, particularly fibrocartilage, articular cartilage, meniscal tissue, and the like, while limiting the depth of necrosis and tissue adjacent to the treatment site. Such apparatus and methods should be amenable to precise control over the energy flux levels applied to the treatment region, and should be able to provide energy densities sufficient to provide rapid cutting and ablation. The devices should be adaptable to a wide variety of purposes, particularly including both small and large electrode surfaces, and rigid and flexible structures which can be used in open surgery, arthroscopic surgery, and other minimally invasive surgical techniques.

2. Description of the Background Art

Devices incorporating radio frequency electrodes for use in electrosurgical and electrocautery techniques are described in Rand et al. (1985) *J. Arthro. Surg.* 1:242–246 and U.S. Pat. Nos. 5,281,216; 4,943,290; 4,936,301; 4,593, 691; 4,228,800; and 4,202,337. U.S. Pat. No. 5,281,216 describes a bipolar device having an active electrode coated with a high impedance material where the differential impedance between the active and return electrodes is optimized to provide a desired cutting effect. Vascular catheters and devices incorporating radio frequency electrodes to assist in penetrating atheroma and plaque are described in U.S. Pat. Nos. 5,281,218; 5,125,928; 5,078, 717; 4,998,933; and 4,976,711, and PCT publications WO 93/20747 and WO 90/07303, the latter of which describes a catheter having four isolated electrode surfaces at its distal end. Electrosurgical power supplies including power controls and/or current limiting systems are described in U.S. Pat. No. 5,267,997 and PCT publication WO 93/20747. Surgical lasers for cutting and ablation in arthroscopic and other procedures are described in Buchelt et al. (1991) Surgery and Medicine II:271–279; and U.S. Pat. Nos. 5,147, 354; 5,151,098; 5,037,421; 4,968,314; 4,785,806; 4,737, 678; 4,736,743; and 4,240,441.

SUMMARY OF THE INVENTION

The present invention provides methods and apparatus for selectively applying electrical energy to structures within a patient's body. The methods and apparatus are particularly useful for performing electrosurgical interventions, such as ablation and cutting of body structures, through the controlled application of high frequency electrical voltages and currents.

Apparatus according to the present invention comprise electrosurgical probes including a shaft having a proximal end, a distal end, an electrode array disposed near the distal end of the shaft, and a connector disposed near the proximal end of the shaft. The shaft will be of a type suitable for use in open and/or minimally invasive surgical procedures, such as arthroscopic, laparoscopic, thoracoscopic, and other endoscopic procedures. The shaft may be rigid, flexible, or include both rigid and flexible portions, and will be generally suitable for manipulation by the treating physician from the proximal end. A common electrode may optionally be provided on the shaft, typically being mounted over the exterior of the shaft and spaced proximally from the electrode array, and preferably being covered with a perforate, electrically non-conductive shield to protect against accidental tissue contact. The electrode array includes a plurality of electrically isolated electrode terminals disposed over a contact surface, which may be a planar or non-planar surface and which may be located at the distal tip or over a lateral surface of the shaft, or over both the tip and lateral surface (s). Such electrode arrays are particularly useful for performing electrosurgical ablation, as described in more detail below. In addition to planar and other surfaces, the electrode array may be arranged in a linear pattern, which is particularly useful as a blade for electrosurgical cutting procedures. The electrode array will include at least two and preferably more electrode terminals, and may further comprise a temperature sensor. The connector permits electrical coupling of the electrode terminals, and optionally temperature sensor, to a high frequency power supply and optionally temperature monitor and/or controller for operation of the probe.

The use of such electrode arrays in electrosurgical procedures is particularly advantageous as it has been found to limit the depth of tissue necrosis without substantially reducing power delivery and ablation rates. Heretofore, increased power delivery with electrosurgical devices has generally been achieved by increasing monolithic electrode area. The resulting large electrode surfaces, however, cause tissue necrosis to a depth which varies proportionally with the width and area of the electrode surface. The present invention provides a more controlled necrosis depth by utilizing a plurality of isolated electrode terminals, where the terminals are preferably laterally spaced-apart by a distance from one-tenth to one terminal diameter, with spacing between larger electrode terminals generally being at the lower end of the range. Such spacing provides adequate power delivery and ablation rates without excessive tissue necrosis, which is usually limited to a depth less than one electrode terminal diameter.

Apparatus according to the present invention further include an electrosurgical high frequency power supply comprising a multiplicity of independent current sources and a connector which mates with a corresponding connector on the electrosurgical probe. The current sources preferably comprise passive or active current limiting circuit structures in parallel with each other and in series with a common voltage source within the power supply. Passive current limiting circuit structures may include inductor(s), capacitor(s), and/or resistor(s) in known circuit configurations. In all cases, the passive current limiting structures will be designed to limit current flow when the associated electrode terminal is in contact with a low resistance return path back to the common or return electrode. Preferred passive current limiting structures comprise (1) inductors in series with each electrode terminal and
(2) capacitors in series and inductors in parallel with each electrode terminal, as described in detail hereinafter.

Active current limiting circuit structures will usually comprise a switching element to turn off current flow whenever the associated electrode terminal contacts a low (or in some instances high) impedance return path back to the common or return electrode. The switching element could be mechanical, e.g., a relay, but preferably will be solid state, e.g., a silicon controlled rectifier (SCR) or silicon controlled switch (SCS). The switch will be turned on and off by a controller which can detect the low resistance path (typically by sensing current flow above a threshold value). The controller can be implemented in hardware or software, typically being part of the power supply.

The high frequency electrosurgical power supply optionally includes a temperature controller which is connected to the temperature sensor on the electrosurgical probe and which adjusts the output voltage of the voltage source in response to a temperature set point and the measured temperature value received from the probe. In this way, the power output and temperature may be controlled while the individual current sources limit or block the power output from corresponding individual electrode terminals. Such limitation of individual electrode terminal power outputs is critical to limiting energy loss from the electrode array as described in more detail below.

The present invention still further provides an electrosurgical system including both the electrosurgical probe and electrosurgical power supply as described above.

According to the method of the present invention, an electrosurgical probe is positioned adjacent to a body structure so that an electrode array is brought into at least partial contact with the structure. The electrode array includes a plurality of isolated electrodes, and a high frequency voltage is applied between the electrode array and the patient's body. The voltage causes current flow between each electrode terminal and the body structure which is contacted by the electrode terminal, where current flow through all low electrical impedance paths is preferably but not necessarily limited. It will be appreciated that such low impedance paths generally occur when an electrode terminal does not contact the body structure, but rather is in contact with a low impedance environment, such as saline, blood, or other electrolyte. The presence of an electrolyte provides a relatively low impedance path back to the common or return electrode, which may be on the electrosurgical probe or may be attached externally to the patient. Such electrosurgical methods are particularly useful when a region is to be flushed with saline, such as in an electrosurgical ablation of fibrocartilage, articular cartilage, meniscal tissue, and the like, in arthroscopic procedures.

In some cases, it may be desirable to provide current limitation or control when individual electrode terminals contact very high resistance body structures, such as bone, cartilage (which has a higher resistivity than meniscus and other tissues), and the like. Current limitation when the electrode terminals contact high resistance structures will usually require active control schemes (i.e., as passive control circuitry will be inadequate), and it will be possible to provide control protocols where current can be limited when it either exceeds or falls below an expected range characteristic of the target tissue to be treated.

A further understanding of the nature and advantages of the invention will become apparent by reference to the remaining portions of the specification and drawings.

BRIEF DESCRIPTION OF THE DRAWINGS

FIG. 8 is a perspective view of an electrosurgical probe with the electrode array disposed at a right angle to the axis of shaft of probe.

FIG. 9 is a perspective view of an electrosurgical probe with electrode arrays disposed on the lateral and tip surfaces at the distal end of the probe.

FIG. 10 is a perspective view of the distal end of an electrosurgical probe with an atraumatic shield extending distally from the electrode array.

FIG. 11 illustrates use of the probe of FIG. 10 in ablating target tissue.

FIG. 12 is a detailed end view of an electrosurgical probe having an elongate, linear array of electrode terminals suitable for use in surgical cutting.

FIG. 13 is a detailed view of a single electrode terminal having a flattened end at its distal tip.

FIG. 14 is a detailed view of a single electrode terminal having a pointed end at its distal tip.

FIG. 15 is a detailed view of a single electrode terminal having a square end at its distal tip.

DESCRIPTION OF THE PREFERRED EMBODIMENT

Figure 1:
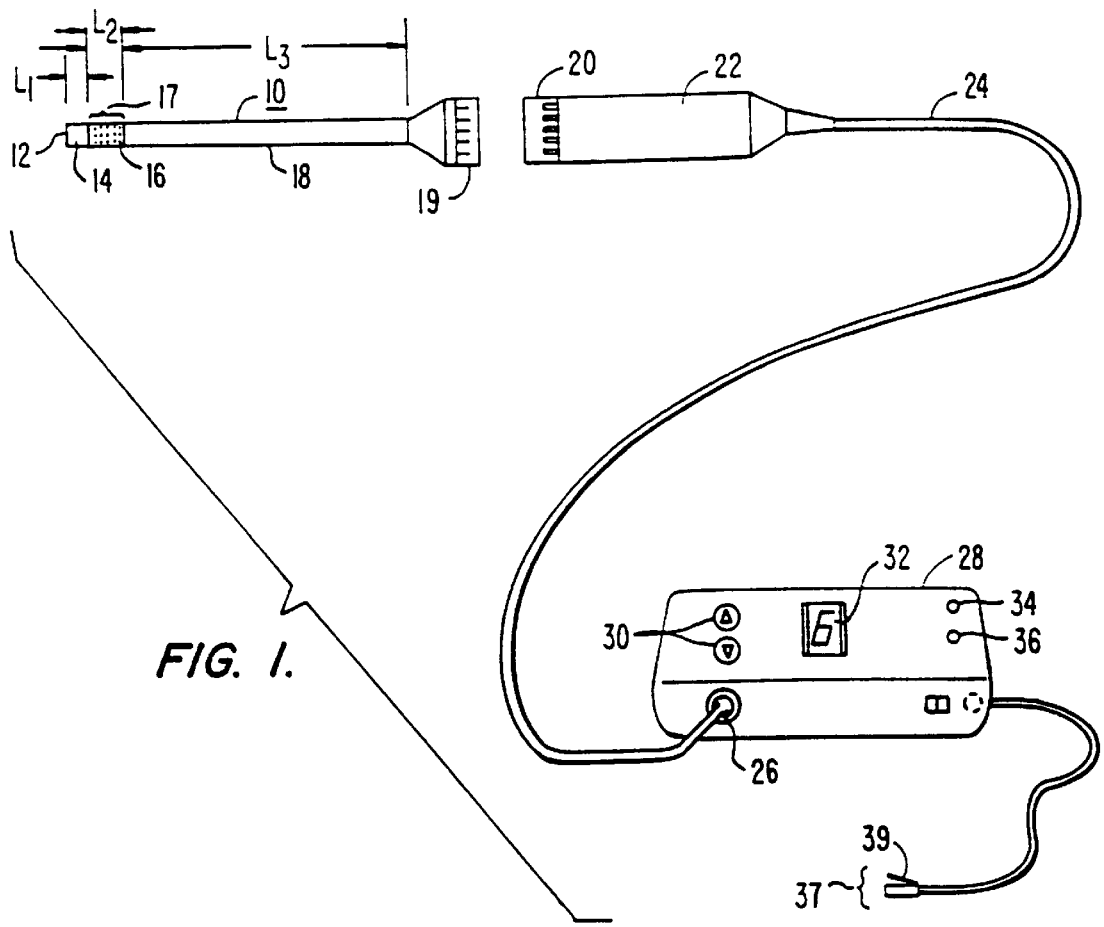
FIG. 1 is a perspective view of the electrosurgical system including an electrosurgical probe and electrosurgical power supply constructed in accordance with the principles of the present invention.

The present invention provides a method and apparatus for selectively heating a target location within a patient's body, such as solid tissue or the like, particularly including articular cartilage, fibrocartilage, meniscal tissue, and the like. In addition to articular cartilage and fibrocartilage, tissues which may be treated by the method and apparatus of the present invention include tumors, abnormal tissues, and the like. For convenience, the remaining disclosure will be directed specifically at the cutting, shaping or ablation of fibrocartilage and articular cartilage during arthroscopic or endoscopic procedures but it will be appreciated that the apparatus and methods can be applied equally well to procedures involving other tissues of the body, as well as to other procedures including open surgery, laparoscopic surgery, thoracoscopic surgery, and other endoscopic surgical procedures.

The target tissue will be, by way of example but not limited to, articular cartilage, fibrocartilage, and meniscal tissue, such as found in the joints of the knee, shoulder, hip, foot, hand and spine. The present invention uses an electrode array including a plurality of independently current-limited and/or power-controlled electrode terminals distributed over a distal contact surface of a probe to apply heat selectively to the target tissue while limiting the unwanted heating of the surrounding tissue and environment resulting from power dissipation into surrounding electrically conductive liquids, such as blood, normal saline, and the like.

The electrosurgical probe will comprise a shaft having a proximal end and a distal end which supports an electrode array near its distal end. The shaft may assume a wide variety of configurations, with the primary purpose being to mechanically support the electrode array and permit the treating physician to manipulate the array from a proximal end of the shaft. Usually, the shaft will be a narrow-diameter rod or tube, more usually having dimensions which permit it to be introduced through an associated trocar or cannula in a minimally invasive procedure, such as arthroscopic, laparoscopic, thoracoscopic, and other endoscopic procedures. Thus, the shaft will typically have a length of at least 10 cm, more typically being 25 cm, or longer, and will have a diameter of at least 1 mm, usually being at least 2 mm, and frequently being in the range from 2 to 10 mm. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft. Specific shaft designs will be described in detail in connection with the figures hereinafter.

The electrode array have an area in the range from 0.01 $mm^2$ to 2.5 $cm^2$, preferably from 0.025 $mm^2$ to 1 $cm^2$, more preferably from 0.25 $mm^2$ to 50 $mm^2$, and often from 0.5 $mm^2$ to 25 $mm^2$, and will usually include at least two isolated electrode terminals, more usually at least four electrode terminals, preferably at least six electrode terminals, more preferably at least eight electrode terminals, even more preferably at least 15 electrode terminals, and still more preferably at least 20 electrode terminals, and often 50 or more electrode terminals, disposed over the distal contact surfaces on the shaft. By contacting the electrode array(s) on the contact surface(s) against target tissue and applying high frequency voltage between the array(s) and an additional common or return electrode in direct or indirect contact with the patient's body, the target tissue is selectively ablated or cut, permitting selective removal of portions of the target tissue while desirably minimizing the depth of necrosis to surrounding tissue. In particular, this invention provides a method and apparatus for effectively ablating and cutting articular cartilage and fibrocartilage by simultaneously applying both (1) electrical energy to the target tissue surrounding and immediately adjacent to the tip of the probe and (2) pressure against the target tissue using the probe itself.

Each individual electrode terminal in the electrode array is electrically insulated from all other electrode terminals in the array within said probe and is connected to a power source which is isolated from each of the other electrodes in the array or to circuitry which limits or interrupts current flow to the electrode when low resistivity material (e.g., blood or electrically conductive saline irrigant) causes a lower impedance path between the common electrode and the individual electrode terminal. The isolated power sources for each individual electrode may be separate power supply circuits having internal impedance characteristics which limit power to the associated electrode terminal when a low impedance return path is encountered or may be a single power source which is connected to each of the electrodes through independently actuable switches.

The tip region of the probe is thus composed of many independent electrode terminals designed to deliver electrical energy in the vicinity of the tip. The selective heating of the target tissue is achieved by connecting each individual electrode terminal and the common electrode (e.g., a band of conductive material proximal to the electrode array at the tip or an external electrode which is placed on the outside of the patient's body) to a power source having independently controlled or current-limited channels. The application of high frequency voltage between the common electrode and the electrode array results in the conduction of high frequency current from each individual electrode terminal to the said common electrode. The current flow from each individual electrode terminal to the common electrode is controlled by either active or passive means, or a combination thereof, to deliver electrical energy to the target tissue while minimizing energy delivery to surrounding (non-target) tissue and any conductive fluids which may be present (e.g., blood, electrolytic irrigants such as saline, and the like).

In a preferred aspect, this invention takes advantage of the differences in electrical resistivity between the target tissue (e.g., articular cartilage or fibrocartilage) and the surrounding conductive liquid (e.g., isotonic (normal) saline irrigant). By way of example, for any selected level of applied voltage, if the electrical conduction path between the common electrode and one of the individual electrode terminals within the electrode array is isotonic saline irrigant liquid (having a relatively low electrical resistivity), said current control means connected to the individual electrode will limit current flow so that the heating of intervening conductive liquid is minimized. In contrast, if a portion of or all of the electrical conduction path between the common electrode and one of the individual electrode terminals within the electrode array is articular cartilage or fibrocartilage (having a relatively higher electrical resistivity), said current control circuitry or switch connected to said individual electrode will allow current flow sufficient for the heating or ablation or electrical breakdown of the target tissue in the immediate vicinity of the electrode surface.

The application of a high frequency voltage between the common or return electrode and the electrode array for appropriate time intervals effects ablation, cutting or reshaping of the target tissue. The tissue volume over which energy is dissipated (i.e., a high voltage gradient exists) may be precisely controlled, for example, by the use of a multiplicity of small electrodes whose effective widths (i.e., diameters for round wire terminals) range from about 0.05 mm to 2 mm, preferably from about 0.1 mm to 1 mm. Electrode terminal areas for both circular and non-circular terminals will have a contact area below 5 mm, preferably being in the range from 0.001 $mm^2$ to 2 $mm^2$, and more preferably from 0.01 $mm^2$ to 1 $mm^2$. The use of small electrode terminals reduces the extent and depth of tissue necrosis as a consequence of the divergence of current flux lines which emanate from the exposed surface of each electrode terminal. Energy deposition in tissue sufficient for irreversible damage (i.e., necrosis) has been found to be limited to a distance of about one-half to one electrode terminal diameter. This is a particular advantage over prior electrosurgical probes employing single and/or larger electrodes where the depth of tissue necrosis may not be sufficiently limited. Heretofore, increased power application and ablation rates would usually be achieved by increasing the electrode area. Surprisingly, with the present invention, it has been found that the total electrode area can be increased (to increase power delivery and ablation rate) without increasing depth of necrosis by providing multiple small electrode terminals. Preferably, the terminals will be spaced-apart by a distance in the range from one-tenth diameter to one diameter for optimum power delivery, with smaller spacing between larger terminals. The depth of necrosis may be further controlled by switching the applied voltage off and on to produce pulses of current, said pulses being of sufficient duration and associated energy density to effect ablation and/or cutting while being turned off for periods sufficiently long to allow for thermal relaxation between energy pulses. In this manner, the energy pulse duration, magnitude and the time interval between energy pulses are selected to achieve efficient rates of tissue ablation or cutting while allowing the temperature of the heated zone of tissue to "relax" or return to normal physiologic temperatures before the onset of the next energy (current) pulse.

The rate of energy delivery to the target tissue is controlled by the applied voltage level and duty cycle of the voltage pulse. The use of high frequency current minimizes induced stimulation of muscle tissue or nerve tissue in the vicinity of the body structure being treated. In addition, high frequencies minimize the risk of interfering with the natural pacing of the heart in circumstances where the probe of the present invention is used near the heart.

The power applied to the common electrode and the electrode array will be at high or radio frequency, typically between about 20 kHz and 20 MHz, usually being between about 30 kHz and 1 MHz, and preferably being between about 50 kHz and 400 kHz. The RMS (root mean square) voltage applied will usually be in the range from about 5 volts to 1000 volts, preferably being in the range from about 50 volts to 800 volts, and more preferably being in the range from about 10 volts to 500 volts. Usually, the current level will be selectively limited or controlled and the voltage applied will be independently adjustable, frequently in response to the resistance of tissues and/or fluids in the pathway between an individual electrode and the common electrode. Also, the applied current level may be in response to a temperature control means which maintains the target tissue temperature with desired limits at the interface between the electrode arrays and the target tissue. The desired surface temperature of the target tissue will usually be in the range from about 40° C. to 500° C., and more usually from about 50° C. to 300° C.

The preferred power source of the present invention delivers a high frequency current selectable to generate average power levels ranging from tens of milliwatts to tens of watts per electrode, depending on the target tissue being heated, the rate of ablation desired or the maximum allowed temperature selected for the probe tip. The power source allows the user to select the current level according to the specific requirements of a particular arthroscopy procedure or other endoscopic procedure.

The power source will be current limited or otherwise controlled so that undesired heating of electrically conductive fluids or other low electrical resistance tissues does not occur. In a presently preferred embodiment of the present invention, current limiting inductors are placed in series with each independent electrode terminal, where the inductance of the inductor is selected to provide high impedance at the frequency of operation. Alternatively, capacitor-inductor (CL) circuit structures may be employed, as described in more detail below. Additionally, a current limiting resistor may be selected having a large positive temperature coefficient of resistance so that, as the current level begins to rise for any individual electrode in contact with a low resistance medium (e.g., saline irrigant), the resistance of the current limiting resistor increases significantly, thereby minimizing the power delivery from said electrode into the low resistance medium (e.g., saline irrigant). Thus, the electrode terminal sees a relatively constant current source so that power dissipation through a low resistance path, e.g., normal saline irrigant, will be substantially diminished.

As an alternative to such passive circuit structures, constant current flow to each electrode terminal may be provided by a multi-channel power supply. A substantially constant current level for each individual electrode terminal within a range which will limit power delivery through a low resistance path, e.g., isotonic saline irrigant, would be selected by the user to achieve the desired rate of cutting or ablation. Such a multi-channel power supply thus provides a constant current source with selectable current level in series with each electrode terminal, wherein all electrodes will operate at or below the same, user selectable maximum current level. Current flow to all electrode terminals could be periodically sensed and stopped if the temperature measured at the surface of the electrode array exceeds user selected limits. Particular control system designs for implementing this strategy are well within the skill of the art.

Yet another alternative involves the use of one or several power supplies which allow one or several electrodes to be simultaneously energized and which include active control means for limiting current levels below a preselected maximum level. In this arrangement, only one or several electrodes would be simultaneously energized for a brief period. Switching means would allow the next one or several electrodes to be energized for a brief period. By sequentially energizing one or several electrodes, the interaction between adjacent electrodes can be minimized (for the case of energizing several electrode positioned at the maximum possible spacing within the overall envelope of the electrode array) or eliminated (for the case of energizing only a single electrode at any one time). As before, a resistance measurement means may be employed for each electrode prior to the application of power wherein a (measured) low resistance (below some preselected level) will prevent that electrode from being energized during given cycle. By way of example, the sequential powering and control scheme of the present invention would function in a manner similar to an automobile distributor. In this example, an electrical contact rotates past terminals connected to each spark plug. In this example, each spark plug corresponds to the exposed surface of each of the electrodes. In addition, the present invention includes the means to measure the resistance of the medium in contact with each electrode and cause voltage to be applied only if the resistance exceeds a preselected level.

The electrode array is formed over a contact surface on the shaft of the electrosurgical probe. The area of the contact surface can vary widely, and the contact surface can assume a variety of geometries, with particular areas in geometries being selected for specific applications. Electrode array contact surfaces will have areas as set forth above and can be planar, concave, convex, hemispherical, conical, or virtually any other regular or irregular shape. Most commonly, the electrode arrays will be formed at the distal tip of the electrosurgical probe shaft, frequently being planar, disk-shaped, or hemispherical surfaces for use in reshaping procedures or being linear arrays for use in cutting. Alternatively or additionally, the electrode arrays may be formed on lateral surfaces of the electrosurgical probe shaft (e.g., in the manner of a spatula), facilitating access to certain body structures in electrosurgical procedures.

Figure 2:
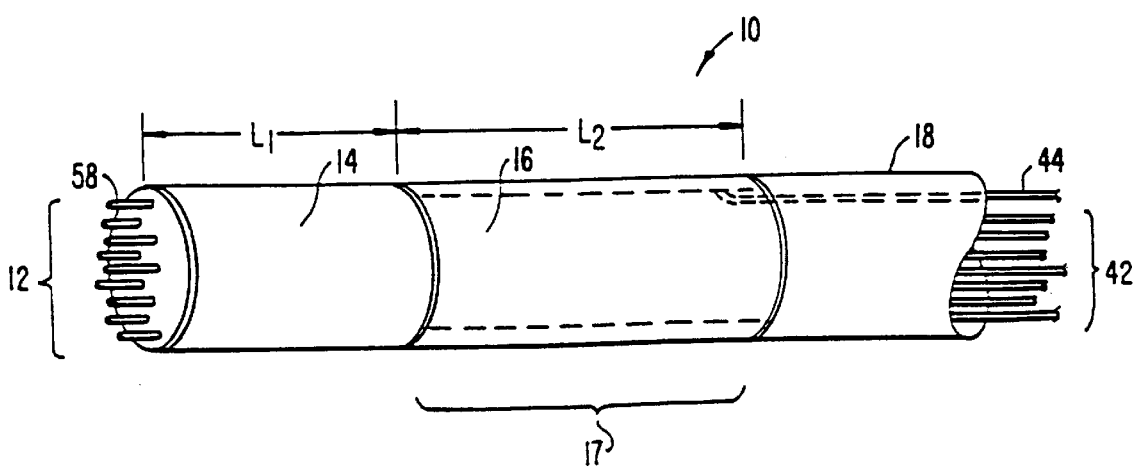
FIG. 2 is an enlarged, detailed view of the distal tip of the electrosurgical probe of FIG. 1.

In an exemplary embodiment as shown in FIG. 1, a probe 10 includes an elongated shaft 13 which may be flexible or rigid, with flexible shafts optionally being disposed with support cannulas or other structures (not shown). Referring to FIGS. 1 and 2, the probe 10 includes an array of electrode terminals 58 disposed on the distal tip 12 of shaft 13. The electrode terminals 58 are electrically isolated from each other and from a common or return electrode 17 which is disposed on the shaft proximally of the electrode array, preferably being with 1 mm to 25 mm of the distal tip 12. Proximally from the tip 12, the return electrode 17 is generally concentric with the shaft of the probe 10. Said probe 10 may be constructed having zones of varying flexibility (or conversely, stiffness) along the probe length. It is advantageous, for example, to have greater flexibility (i.e., lesser stiffness) at the distal end of the probe 10 (region $L_3$ in FIG. 1) in order to increase the capability of the probe to gain access to operative sites which are not in a direct line path with the entrance site into the body cavity. In the preferred embodiment illustrated in FIG. 1, probe 10 would have two or three regions wherein regions $L_1$ and $L_2$ are stiffer than region $L_3$. The preferred length for region $L_1$ is in the range from 0.5 mm to 25 mm, for region $L_2$ is in the range from 1 mm to 20 mm, and for region $L_3$ is from 5 cm to 25 cm.

Still referring to FIGS. 1 and 2, each of the terminals 58 is connected to an active or passive control network within a power source and controller 28 by means of the individually insulated conductors 42. The proximal portion of the probe 10 is also equipped with a connector 19 which can be removably connected to a connector 20 in a reusable handle 22. The proximal portion of the handle 22 and cable 24 also has a connector 26 for providing the electrical connections to the controller 28.

Referring to FIG. 1, the power source and controller 28 provides high frequency voltage to the electrode terminals 28 (of FIG. 2) by means of a cable 24 from connector 20 in handle 22 to receptacle 26, the power source and controller 28. The power source and controller 28 has a selector 30 to change the applied voltage level. A conductor 44 extends from the common electrode 17 (FIG. 2) and is connected to the power source and controller 28 by the same cable 24. The power source and controller 28 also includes the means for energizing the electrodes 58 of probe 10 through the depression of foot pedal 39 in a foot pedal 37 positioned close to the user. The assembly 37 may also include a second pedal (not shown) for remotely adjusting the energy level applied to electrodes 58.

Figure 3:
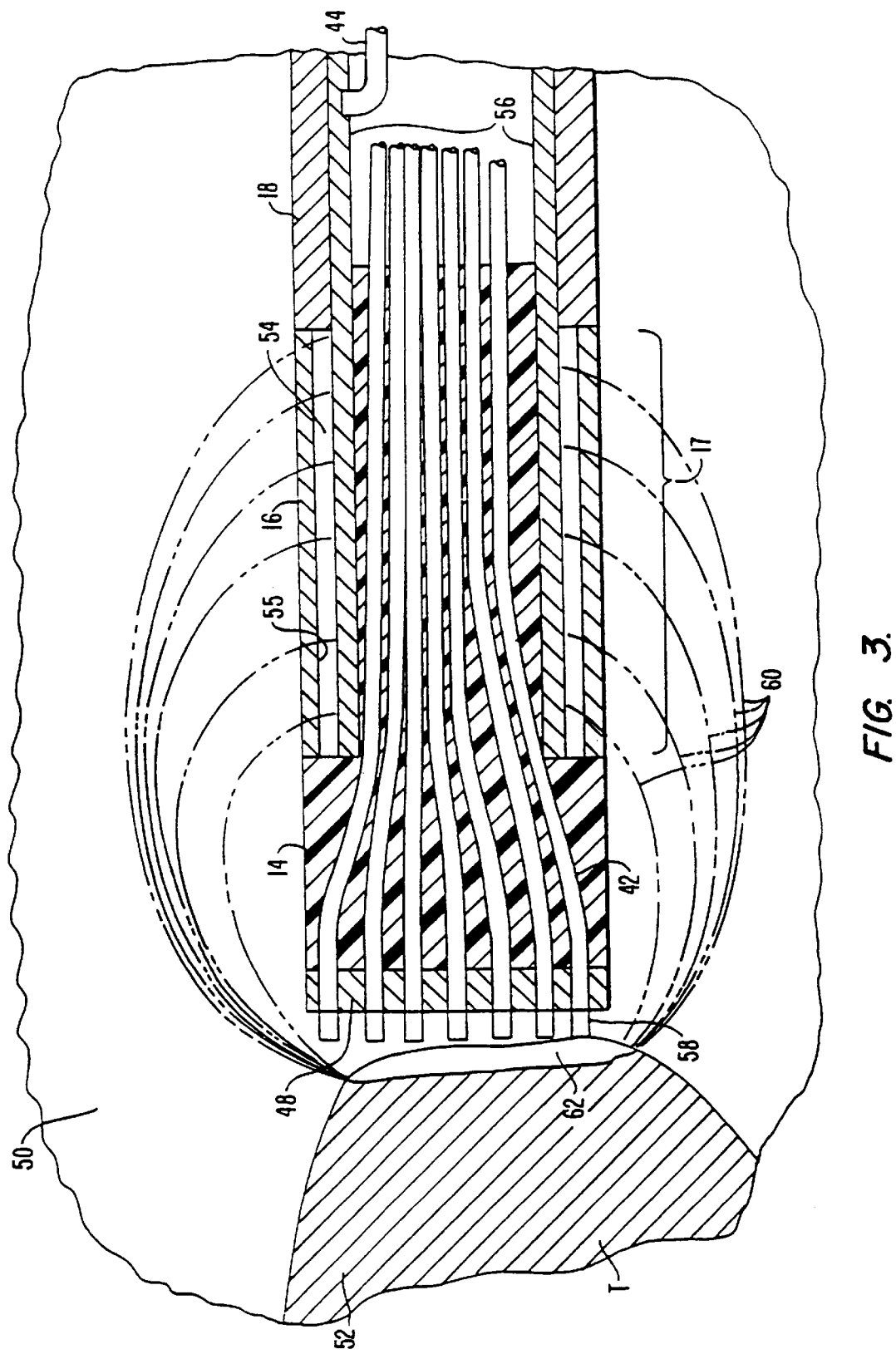
FIG. 3 is a cross-sectional view of the distal tip of the electrosurgical probe of FIGS. 1 and 2.

Referring to FIG. 2 and FIG. 3, the distal tip 12 of probe 10 in the preferred embodiment contains the exposed surfaces of the electrode terminals 58. The electrode terminals 58 are secured in a matrix 48 of suitable insulating material (e.g., ceramic or glass) which could be formed at time of manufacture in a flat, hemispherical or other shape according to the requirements of a particular procedure. Proximal to the distal tip 12, the isolated electrode wires 42 are contained in an insulating insert 14 (FIG. 3) of generally cylindrical shape extending from matrix 48 and into a tubular support member 56.

Referring to FIGS. 2 and 3, the tubular support member 56 is preferably formed from an electrically conductive material, usually metal, and is disposed within an electrically insulative jacket 18. The electrically conductive tubular support member 56 defines the common or return electrode 17 with respect to the array of individual electrodes 12 in order to complete the electrical circuit such that current will flow between each individual electrode 58 and the common electrode structure 17. The common electrode 17 is located near the distal tip 12 of probe 10. The insulating insert 14 distal to the common electrode 17 is composed of an electrically insulating material such as epoxy, plastic, ceramic, glass or the like. The electrically conductive tubular support member 56 will preferably be sufficiently rigid to provide adequate column strength to manipulate body structures with the shaft of probe 10. The tubular member 56 is composed of a material selected from the group consisting of stainless steel, titanium or its alloys, molybdenum or its alloys, and nickel or its alloys. The electrically conductive tubular member 56 will preferably be composed of the same metal or alloy which forms the electrode terminals 58 to minimize any potential for corrosion or the generation of electrochemical potentials due to the presence of dissimilar metals contained within an electrically conductive fluid 50 such as isotonic saline commonly used as an irrigant for the intended applications.

Referring now to FIGS. 2 and 3, the common electrode terminal structure 17 includes a perforate shield 16 formed from an electrically insulating material which is porous or which contains openings which allow a surrounding electrically conducting liquid 50 (e.g., isotonic saline) to contact the electrically conductive layer 54 which is electrically coupled to the tubular member 56. As shown in FIG. 3, an annular gap 54 may be provided between electrically insulating member 16 and common electrode member 56. Proximal to the common electrode region 17, the tubular member 56 is covered over its entire circumference by the electrically insulating jacket 18, which is typically formed as one or more electrically insulative sheaths or coatings, such as polytetrafluoroethylene, polyimide, and the like. The annular gap 54 preferably has capillary dimensions to maximize fluid contact even when the common electrode terminal structure 17 is not fully immersed in the electrically conductive liquid.

The provision of the electrically insulative jacket 16 over the common electrode structure 17 prevents direct electrical contact between the surface of tubular member 56 and any adjacent body structure. Such direct electrical contact between a body structure (e.g., tendon) and an exposed common electrode member 56 could result in unwanted heating and necrosis of the structure at the point of contact. As shown in FIG. 3, any contact between the common electrode structure 17 (including perforate shield 16) and a body structure will only result in the passage of relatively low current density flux lines 60, thereby minimizing the Joulean heating which could occur in any adjacent body structure. Referring to FIGS. 1 and 3, electrical communication between tubular member 56 and the connector 19 may be provided by an electrically conducting lead wire 44.

The electrode terminals 58 are electrically insulated from each other and are secured together in an array by the electrically insulating matrix 48. The insulating matrix 48 may be ceramic, glass or other high-temperature insulating material. Proximal to the distal tip 12, the electrode wires 42 are covered with an electrically insulating material (e.g., polyimide) and are contained in tubular member 56 which extends the length of the probe 10. The distal tip 12 end of the probe 10 includes the common electrode structure 17 extending over a length $L_2$ which may range from 1 to 20 mm, preferably being from 2 mm to 20 mm. A tip offset $L_1$ provides a minimum separation between said common electrode 17 and the array of electrodes 12, usually being at least 0.5 mm, more usually being at least 1 mm, and sometimes being 2 mm or greater, and preferably being in the range from 0.5 mm to 2 mm.

A central aspect of the present invention is the ability of the probe 10 to deliver high energy flux levels selectively only to the intended areas, i.e., the target tissue T, and not to surrounding healthy tissue or electrically conducting fluids (e.g., isotonic saline irrigant). Such directed energy transfer results in selective heating of the target tissue which allows the probe to cut, ablate or recontour the target tissue. Referring to FIGS. 2 and 3, when the electrode array 12 of the probe 10 is engaged against a region of target tissue 52, some of the electrode terminals 58 will be in contact with target tissue, while other electrode terminals may be in contact with electrically conducting fluid 50. Each of the electrode terminals 58 experiences an electrical impedance which is characteristic of the material which is disposed between the individual electrode terminals 58 and the common electrode structure 17. The present invention takes advantage of the fact that the electrical impedance (resistivity) of typical target tissue at frequencies of 50 kHz or greater (e.g., fibrocartilage and articular cartilage) is higher by a factor of approximately four or more than that of the surrounding electrically conducting fluid 50 typically used as an irrigant during arthroscopic and endoscopic procedures. Thus, if the current passing through each of the electrode terminals 58 is limited to a preselected maximum value, the regions of higher electrical resistance will generate more Joulean heating (power=$I^2R$, where I is the current through resistance, R) than a region of lower electrical resistance.

In contrast to the present invention, electrosurgical methods and apparatus of the prior art involving a single electrode exhibit substantially reduced effectiveness when a portion of the exposed electrode is in contact with a low-resistance pathway (e.g., isotonic saline irrigant). In those circumstances, the majority of power delivered from the single electrode tip is dissipated within the low resistance electrically conducting fluid, thereby significantly reducing the capability to cut or ablate the target tissue.

Furthermore in accordance with the teachings of the present invention, temperature measurement means may be provided in the distal tip 12 to limit the power delivery if measured temperatures exceed user selected levels. Therefore, by either one or a combination of both means described above the target tissue will be selectively heated up while the conductive liquids will experience a minimal rise in temperature. Thus, the probe 10 will selectively and efficiently cut or ablate the target tissue.

Still referring to FIG. 3, another aspect of the present invention is the restriction of high current densities or fluxes to a confined region 62 as defined by the current flux lines 60. The confinement of the high current densities to a limited region 62 allows healthy tissue nearby to remain at or near normal physiologic temperatures, thereby limiting the depth of necrosis into surrounding or underlying healthy tissue 52 to a depth of approximately one electrode diameter. Alternatively, by energizing only one or several electrode terminals 58 at any one time, the depth of necrosis can be still further reduced since the thermal relaxation time between energy pulses for any specific electrode will serve to further limit the depth of necrosis.

Figure 4:
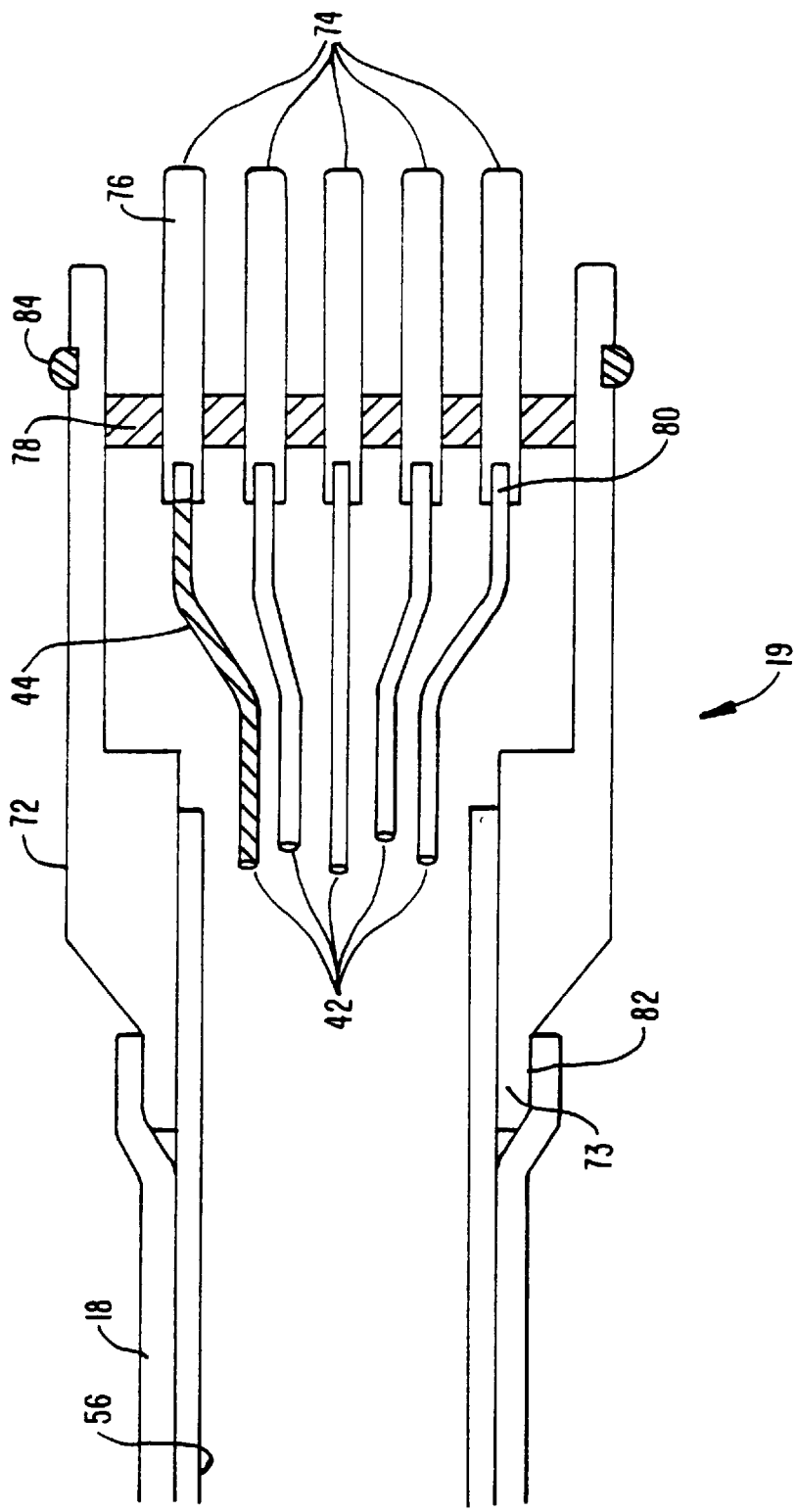
FIG. 4 is a schematic view of a particular connector and lead arrangement which can be employed in the electrosurgical probe of FIGS. 1–3.

Referring to FIGS. 1 and 4, the proximal end of probe 10 includes a connector 19 which includes a multiplicity of electrically conductive pins or contacting member 74 which are in electrical communication with each electrode wire 42. Said electrical communication may be accomplished through mechanical crimping of the terminus of connector pin 74 onto the bare (exposed) electrode lead wire 42 at location 80. Alternatively, the electrode lead wire may be welded, brazed or soldered to the connector pin 74 at location 80. Likewise, the return wire 44 electrically communicating with the common electrode member 56 is connected to one connector pin 76 in a like manner as described above for the electrode leads.

The multiplicity of connector pins 74 and 76 are maintained in a predetermined spaced-apart relationship which corresponds to a mating receptacle 20 at the distal end of the handle 22. The position of the contact pins 74 and 76 is maintained by an electrically insulative member 78 which is secured within a connector housing 72 using adhesives, ultrasonic welding or the like. Alternatively, the connector housing may be overmolded around the connector pin assembly 78 and proximal end of the probe shaft member. In the embodiment shown in FIG. 4, the electrically conductive tubular member 56 is inserted into the distal end of the connector 72 and secured using an adhesive or potting material (e.g., epoxy). The electrically insulative jacket 18 extends from the proximal edge of the common electrode structure 17 to and over an extension 73 at the distal end of the connector housing 72. The electrically insulating jacket 18 thereby effects a liquid tight seal at an interface 82 between the jacket 18 and the connector extension 73. The seal prevents the leakage of electrically conductive liquid (e.g., isotonic saline) into the cavity containing the electrical leads and connector pins which could result in an electrical short between the electrodes and/or between any electrode and the common electrode 17.

Still referring to FIG. 4, a sealing means 84 may also be provided at the proximal end of the connector housing 72 in order to minimize the leakage of electrically conductive liquid (e.g., isotonic saline) at the interface between the connector 19 and the handle connector 20. Said seal member 84 may include a conventional elastomeric o-ring placed in a suitably sized o-ring groove within the connector housing 72.

Figure 5:
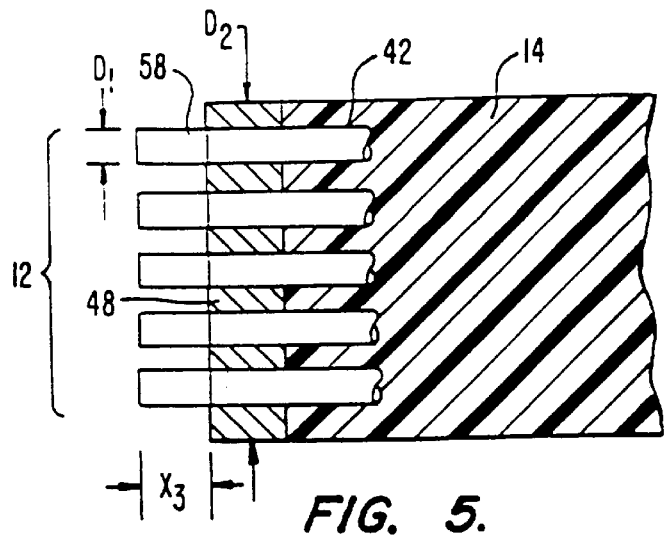
FIG. 5 is a detailed cross-sectional view of the distal end of an electrosurgical probe illustrating an electrode arrangement suitable for rapid cutting and ablation of tissue structures.
Figure 6:
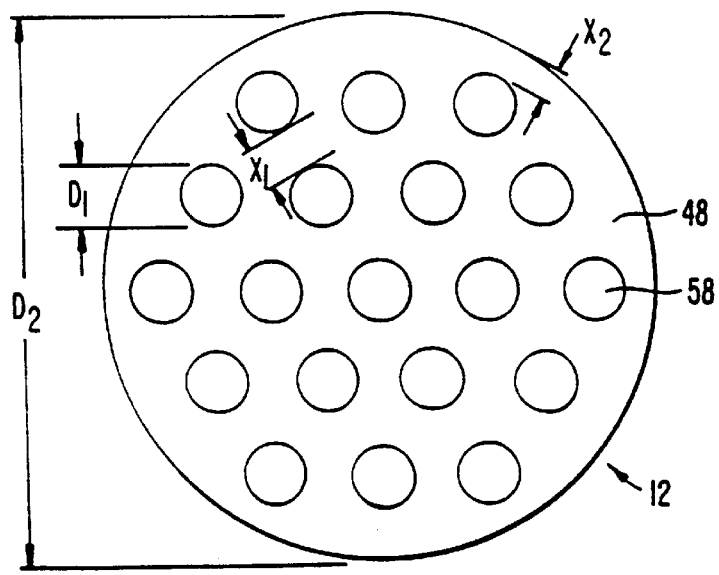
FIG. 6 is a detailed left-end view of the distal end of the electrosurgical probe of FIG. 5.

Referring to FIGS. 5 and 6, an embodiment of the present invention designed for rapid ablation of body structures includes a circular array 12 of electrode terminals 58 maintained in a spaced-apart relationship by electrical insulating matrix 48. For convenience, identical numbering for similar elements will be used for all embodiments. Said electrode terminals 58 may be fabricated using wires having diameters in the preferred range set forth above with an electrically insulating coating extending up to or through the electrically insulating member 48. The regions of the electrode terminals 58 distal to the distal face of the electrically insulating matrix 48 are bare (i.e., no electrically insulating coating) so that the electrode terminals 58 are directly exposed to the surrounding electrically conductive liquid (e.g., isotonic saline) or body structure. The wires and electrode terminals 58 will usually be metals or metal alloys, preferably being selected from the group comprising titanium, tantalum, molybedeum, tungsten, platinum, rhodium, and alloys thereof. The wires and electrode terminals 58 may be solid or may be composites including a core wire which has been coated with one or more of the above metals, compounds or alloys thereof. The electrically insulative matrix 48 may be ceramic or glass or glass/ceramic composition (e.g., alumina, borosilicate glass, quartz glass, or the like).

Still referring to FIGS. 5 and 6, the electrode terminals 58 may extend a distance $X_3$ beyond the distal face of the electrically insulating matrix 48. The extension length $X_3$ may range from 0.05 to 1.0 mm, more preferably being in the range from 0.1 mm to 0.4 mm. The interelectrode spacing $X_1$ ranges from 0.07 mm to 0.4 mm. The electrode terminals 58 may be circular, square, rectangular, triangular or polygonal, or irregular in cross-sectional shape. The characteristic dimension $D_1$ (i.e., diameter in the case of circular electrodes shown in FIG. 6) ranges from 0.1 mm to 0.5 mm depending on the overall size of the probe, the rate of ablation required and the maximum allowed depth of necrosis of the body structure being treated. The overall diameter $D_2$ of the electrode array 12 may range from 0.5 mm to 10 mm, more preferably 1 mm to 5 mm, depending on the particular application and size of the body structure to be treated. In the case of the circular electrode array 12 shown in FIG. 6, the electrode terminals 58 are positioned a small distance $X_2$ from the perimeter of the electrically insulating matrix 48. Said distance $X_2$ is preferably maintained as small as practical to maximize the zone of body structure ablated so that it approximates the diameter $D_2$ of the distal end of the probe 10, thereby permitting the probe to readily engage the body structure to be ablated without mechanical resistance resulting from an excessive border or distance $X_2$ where no ablation has occurred. The distance $X_2$ is preferable less than 0.5 mm and more preferably less than 0.3 mm.

Figure 7:
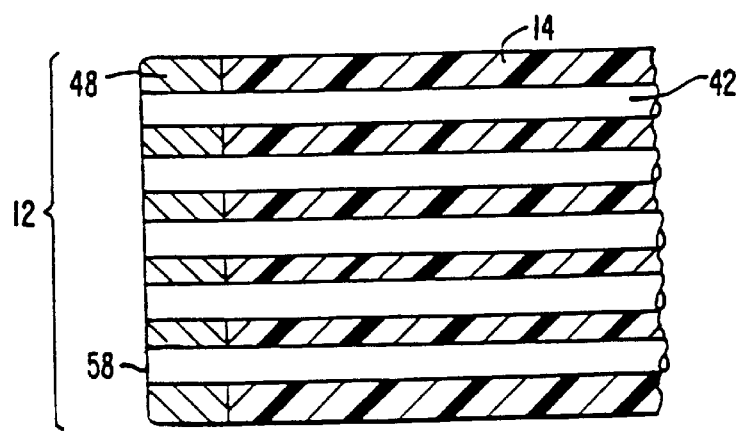
FIG. 7 is a detailed cross-sectional view of the distal end of an electrosurgical probe illustrating an electrode arrangement suitable for smoothing of tissue structures.

Referring to FIG. 7 another embodiment of the present invention intended for smoothing of body structures (e.g., articular cartilage located on the surface of a condyle) while minimizing the depth of necrosis of the underlying tissue includes electrode terminals 58 in an electrical insulating matrix 48 is similar to the array shown in FIGS. 5 and 6 except that the electrode terminals 58 are flush with the surface of the electrically insulating matrix 48. The rate of ablation achievable with the use of "flush" electrode terminals 58 is lower than that for electrodes which extend beyond the face of the electrically insulative matrix 48, but such flush electrode structure can provide a smoother surface on the body structure being treated while minimizing the depth of ablation and necrosis.

Referring to FIG. 8, an alternative configuration of the shaft of a probe 100 is illustrated. This configuration is similar to the electrode array on distal tip 12 of probe 10 and shaft 14 arrangement shown in FIGS. 5 and 7, except that the shaft 14 near the distal end of probe 100 is bent at an angle with respect to the longitudinal axis of the probe. Said angle may range from about 15 degrees to 90 degrees or more depending on the particular tissue structure to be treated. By way of example, the electrode terminal 58 arrangement shown in FIG. 8 allows the electrode array to move over a body structure disposed parallel to the longitudinal axis of the probe 100 with said movement corresponding to forward and backward motion of the probe handle 22. Said electrode terminals 58 may extend beyond the surface of the electrically insulating matrix 48 as shown in FIGS. 5 and 8 or may be flush with the electrically insulating matrix 48 as shown in FIG. 7.

Yet another embodiment of the electrode array of the present invention is illustrated in FIG. 9, wherein electrode terminals 58 are disposed on two (or more) surfaces of the distal end of a probe 120. By way of example, electrode terminals 58a may be located on a lateral surface, spaced-apart by an electrically insulative matrix 48a, and electrodes 58b may be located on the distal tip of the probe 120, spaced-apart by an electrically insulating matrix 48b. The two electrode arrays are supported by an electrically insulating member 82 preferably having rounded atraumatic edges 80 to prevent any unwanted mechanical damage (e.g., abrasion) to the tissue being treated. As described in the previous embodiments, a common electrode structure 17 is disposed proximal to these electrode arrays to provide for the return electrical current path.

Yet another embodiment of the present invention is illustrated in FIGS. 10 and 11. In this embodiment, an electrically insulating shield 74 (or member with electrically insulative coating) extends beyond an array of electrode terminals 58 having a width, length and thickness suitable to allow the electrode terminals 58 at the tip of probe 140 to engage a body structure 52 (e.g., meniscus) while preventing any current flow and related damage to another closely positioned body structure 92 (e.g., the nearby articular cartilage 92 located on the surface of the condyle 90). In this manner, the array of electrode terminal 58 can be brought into close contact with the target tissue 52 without endangering any critical body structures nearby. By way of example, shield 74 may be a metal tab or extension from the probe body which is covered or coated with electrical insulation. Alternatively, the spatula shaped member 74 may be formed by injection molding as an integral portion of the insulating insert 14.

Yet another embodiment is illustrated in FIG. 12 and is designed for cutting of body structures. In this embodiment, the electrode terminals 58 are arranged in a linear or columnar array of one of more closely spaced columns so that as the electrodes 58 are moved along the longer axis (denoted by arrow 160 in FIG. 12), the current flux lines are narrowly confined at the tip of the electrode terminals 58 and result in a cutting effect in the body structure being treated. As before, the current flux lines 60 emanating from the electrode terminals 58 pass through the electrically conducting liquid to the common electrode structure 17 located proximal to the probe tip.

Referring now to FIGS. 13, 14 and 15, several alternative geometries are shown for the electrode terminals 58. These alternative electrode geometries allow the electrical current densities emanating from the electrode terminals 58 to be concentrated to achieve an increased ablation rate and/or a more concentrated ablation effect due to the fact that sharper edges (i.e., regions of smaller radii of curvature) result in higher current densities. FIG. 13 illustrates a flattened extension of a round wire electrode terminal 58 which results in higher current densities at the edges 180. Another example is shown in FIG. 14 in which the electrode terminal 58 is formed into a cone shaped point 182 resulting in higher current densities at the tip of the cone. Yet another example is shown in FIG. 15 in which the electrode 58 is a square wire rather than a round wire. The use of a square wire results in high current densities along each edge 184 which results from the juncture of adjacent faces.

Figure 16:
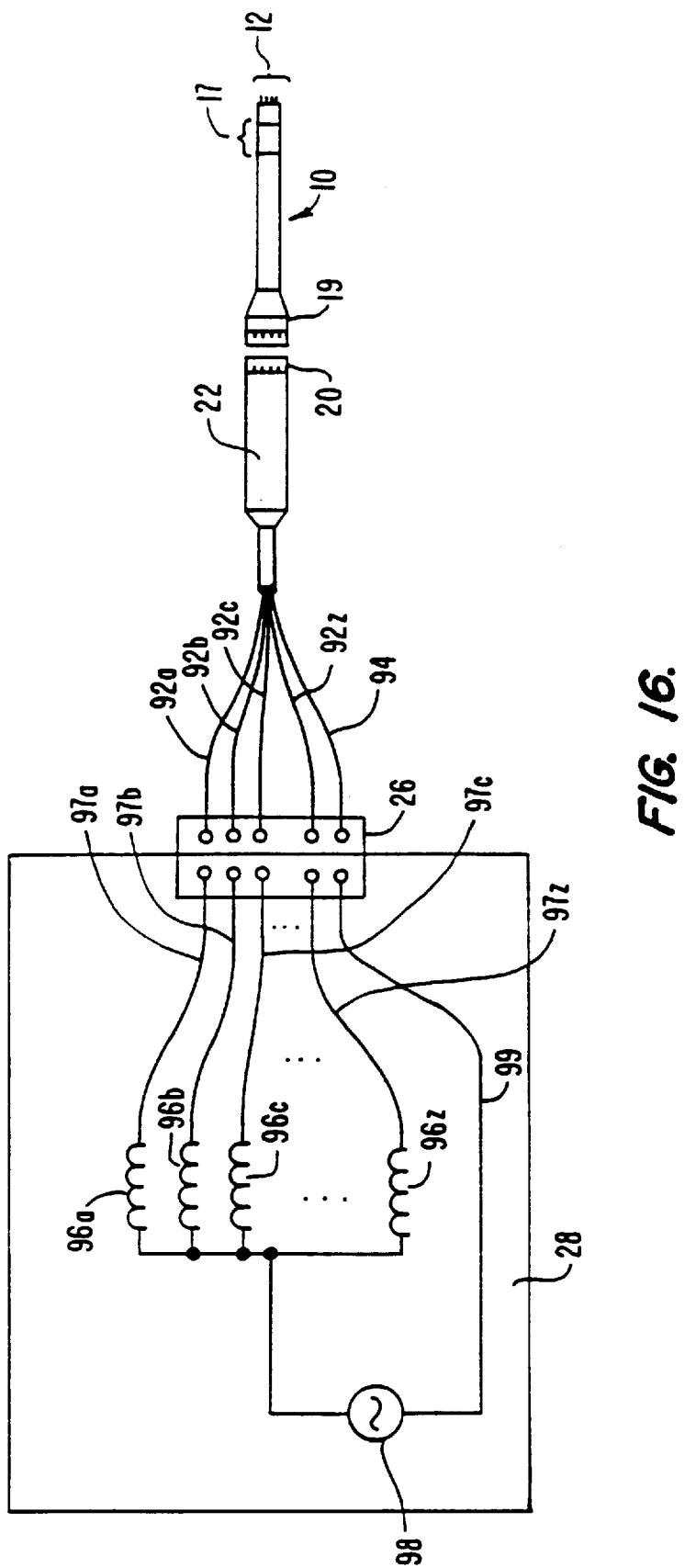
FIGS. 16 and 16A are electrical schematic diagrams illustrating two embodiments of the circuitry of a high frequency power supply constructed in accordance with the principles of the present invention.

Referring to FIG. 16, a high frequency power supply 28 comprises a voltage source 98 which is connected to a multiplicity of current limiting elements 96a, 96b, . . . , 96z, typically being inductors having an inductance in the range from 100 to 5000 microhenries, with the particular value depending on the electrode terminal dimensions, the desired ablation rates, and the like. In the case of ablation of articular and fibrocartilage, suitable inductances will usually be in the range from 50 to 5000 microhenries. Capacitors having capacitance values in the range from 200 to 10,000 picofarads may also be used as the current limiting elements.

Figure 16A:
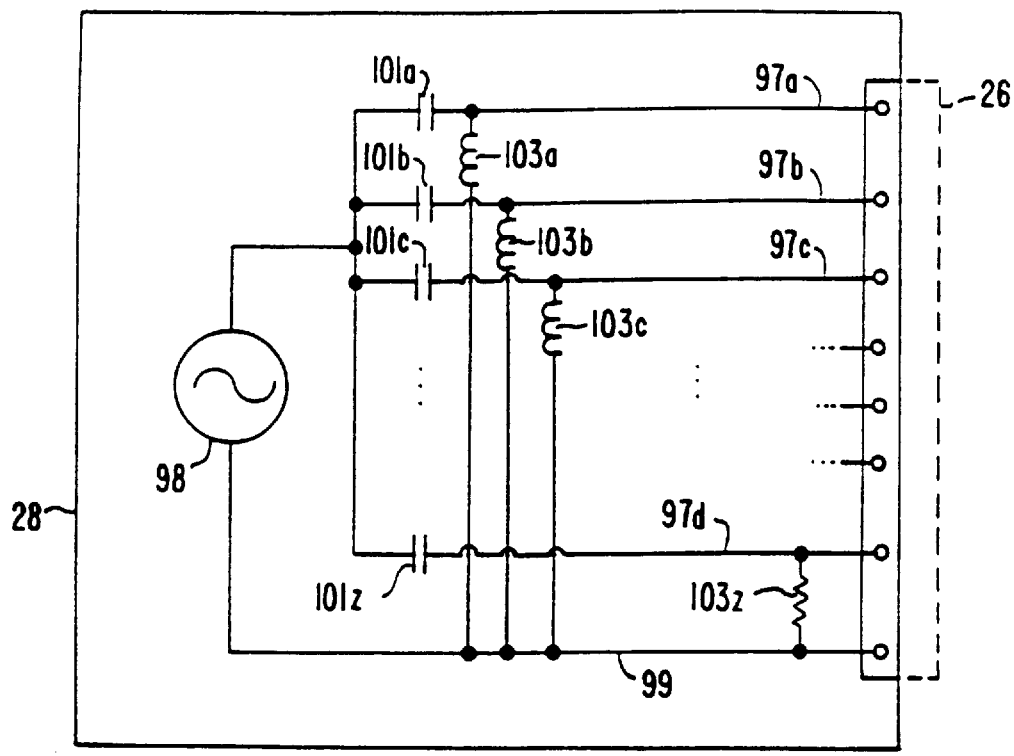

Current limiting elements may also be part of a resonant circuit structure having a capacitor 101 in series with the electrode terminal and an inductor 103 between the electrode lead and the common lead, as illustrated in FIG. 16A. The inductor and capacitor values are selected according to the operating frequency of the voltage source 98. By way of example, at an operating frequency of 100 kHz, current limiting circuit structures may incorporate inductor/capacitor combinations such as (1) 2530 microhenries and 1000 picofarads; (2) 5390 microhenries and 470 picofarads; or (3) 11,400 microhenries and 220 picofarads, respectively.

It would also be possible to use resistors as the current limiting elements. The use of resistors, however, is generally less preferred than use of inductors or capacitor/inductor tuned circuit structures since resistors will have significant $IR^2$ power losses which are generally avoided with the circuits of FIGS. 16 and 16A.

Referring to FIGS. 1, 16, and 16A, each of the individual leads 97 from the current limiting elements 96 and 101/103 are removably connected to leads 92 in cable 24 via connector 26. A common electrode lead 99 from voltage source 98 is removably connected to lead 94 in cable 24 via the same connector 26. Each of the electrode leads 92 and common electrode lead 94 in cable 24 extend into and through handle 22 and terminate in connector 20 located at the distal end of handle 22. As described with reference to FIGS. 3 and 4, electrical leads 92 and common electrode lead 94 connect to electrode leads 42 and common electrode lead 44, respectively, via the interface between removably attachable connectors 19 and 20. In this manner, each of the electrodes in array 12 can be powered by a single voltage source 98 with independent current limiting elements or circuit structures attached to each electrode lead 42 via cable lead 92 and controller lead 96.

Current limitation could alternatively be accomplished by providing a separate power supply and current measuring circuitry for each electrode terminal. Current flow to any electrode terminal which exceeds a preselected (or adjustable) limit would be decreased or interrupted.

Figure 17:
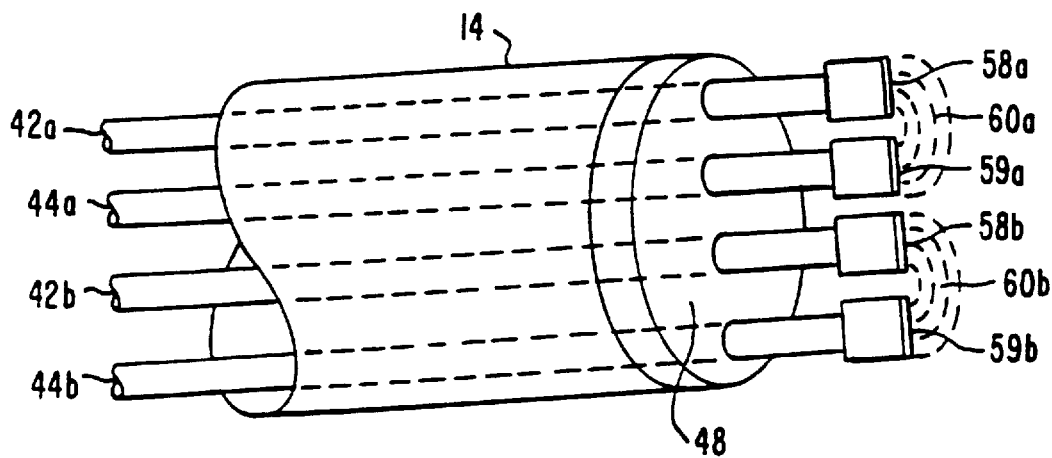
FIG. 17 is a perspective view of the distal end of an electrosurgical probe having an elongate, linear array of electrode terminals.

Another embodiment of the probe of the present invention intended for cutting or ablation of body structures surrounded by electrically conducting liquid (i.e., isotonic saline irrigant) is shown in FIG. 17. Two pairs of electrode terminals 58a/59a and 58b/59b having flattened tips are shown. Leads 58a and 58b are electrically insulated from each other and are individually connected to a separate power source or common voltage supply with independent current limiting circuitry, as discussed above. If an independent power source is used for each pair, then current flow between the electrodes in pair 58a and 59a as well as between the electrodes in pair 58b and 59b. If the leads 44a and 44b from electrodes 59a and 59b are connected to a common electrode 99 in power supply 28, then current will flow between electrode terminals 58a/58b and electrodes 59a/59b. In particular, current will also flow between electrode 58b and 59a. The linear arrangement of electrodes in FIG. 17 is particularly well-suited to rapid cutting of body structures while restricting current flux lines 60 to the near vicinity of the tip of the probe.

Figure 18:
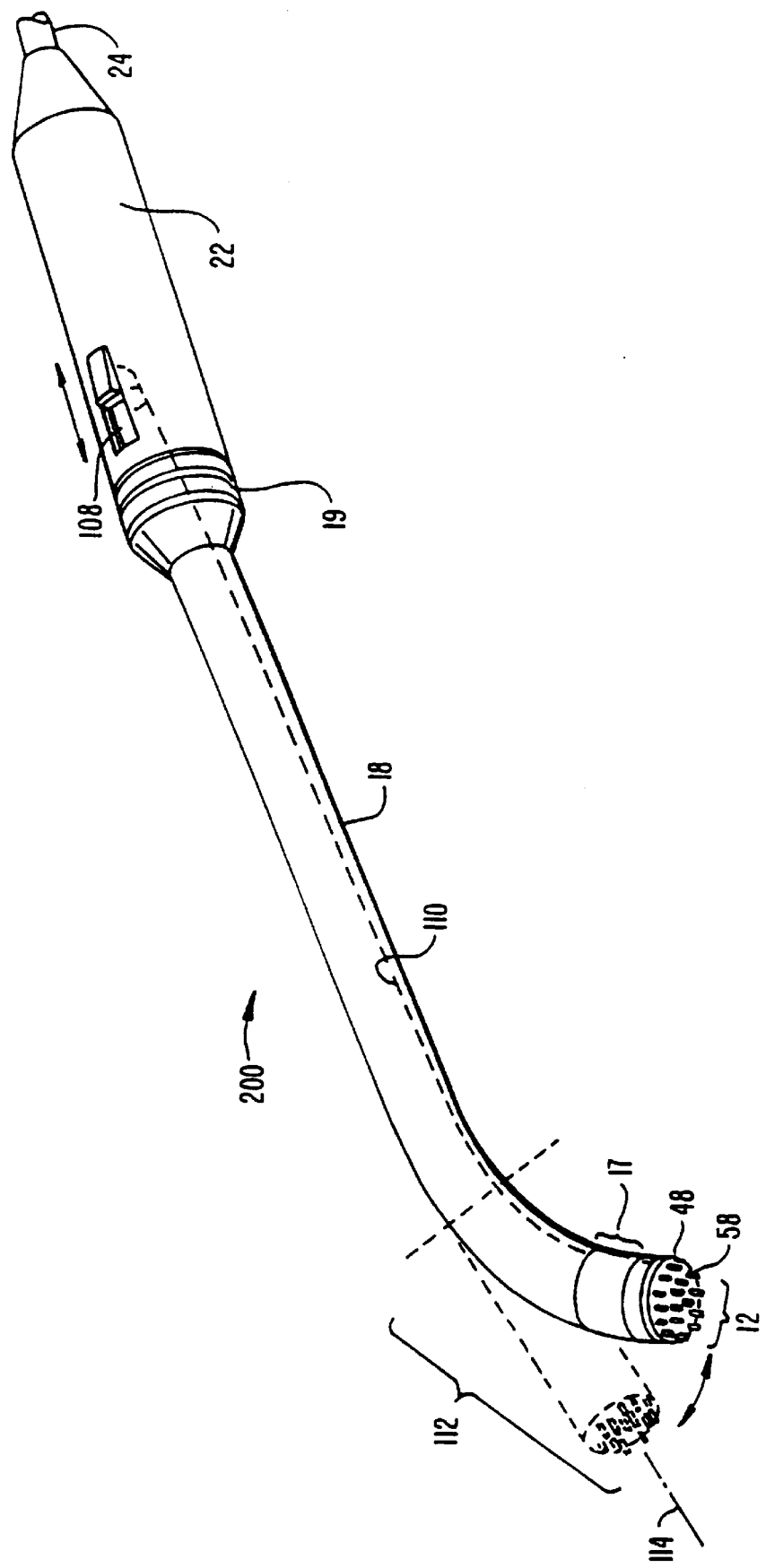
FIG. 18 is a perspective view of the distal end of an electrosurgical probe having a deflectable distal tip.

Another embodiment of the probe of the present invention is illustrated in FIG. 18. The probe 200 contains a flexible distal region 112 which can be deflected relative to a longitudinal axis 114. Such deflection may be selectively induced by mechanical tension, by way of example, through axial translation of thumb slide 108 located on handle 22 which, in turn, increases or decreases tension on a radially offset pull wire 110 connected between the slide and the distal end of the probe 200. Alternatively, a shape memory wire may be used which expands or contracts in response to temperature changes in the wire induced by externally applied heating currents. Thumb slide 108 could be connected to a rheostat (not shown) which would control a heating current through the wire 110, causing the wire to expand or contract depending on the level of the applied current. Said controllable deflection means improves access to body structures in certain surgical situations.

Although the foregoing invention has been described in some detail by way of illustration and example, for purposes of clarity of understanding, it will be obvious that certain changes and modifications may be practiced within the scope of the appended claims.

What is claimed is:

1. An electrosurgical system comprising an electrosurgical probe and an electrosurgical power supply, wherein the electrosurgical probe comprises:
    a shaft having a proximal end and a distal end;
    an electrode array disposed near the distal end of the shaft, said array including a plurality of electrically isolated electrode terminals disposed over a contact surface; and
    a connector near the proximal end of the shaft for electrically coupling the electrode terminals individually to the electrosurgical power supply;
    and wherein the electrosurgical power supply comprises:
        a multiplicity of current limiting elements for independently limiting power to each of the electrode terminals based on impedance at the electrode terminals; and
        a connector which mates with the shaft connector to electrically couple individual ones of said current limiting elements to individual ones of said electrode terminals.

2. An electrosurgical system as in claim 1, wherein the shaft is generally rigid over at least a portion of its length.

3. An electrosurgical system as in claim 1, further comprising a return electrode on the shaft and having an exposed surface area subtantially larger than an exposed surface area of each of the electrode terminals.

4. An electrosurgical system as in claim 3, wherein the return electrode is mounted over the exterior of the shaft and spaced proximally from the electrode array.

5. An electrosurgical system as in claim 1, wherein the electrode array is disposed over the distal tip of the shaft.

6. An electrosurgical system as in claim 1, wherein the electrode array is disposed over a lateral surface of the shaft.

7. An electrosurgical system as in claim 1, wherein the electrode array is arranged in a linear pattern to act as cutting blade.

8. An electrosurgical system as in claim 1, wherein the electrode array includes at least 6 electrode terminals.

9. An electrosurgical system as in claim 1, further comprising a temperature sensor located in the electrode array wherein the connector also electrically couples the temperature sensor to the high frequency voltage source.

10. An electrosurgical system as in claim 1, wherein the current limiting elements comprise current limiting resistors in parallel with each other and in series with a common voltage source.

11. An electrosurgical system as in claim 1, further comprising a temperature controller which adjusts output of the voltage source in response to a temperature set point and a measured temperature value received from the electrosurgical probe through the connector.

12. An electrosurgical apparatus for applying high frequency electrical energy to a tissue structure within or on a patient's body comprising:
    an electrosurgical probe comprising a shaft with a proximal end, a distal end and at least one electrode terminal at or near the distal end;
    an electrosurgical power supply coupled to the electrode terminal for applying a high frequency voltage to the electrode terminal, the power supply having an operating frequency of about 50 kHz to about 300 kHz; and
    a connector coupling the electrode terminal to the power supply for applying voltage to a tissue structure at the operating frequency.

13. The system of claim 12 wherein the power supply has an operating frequency of about 100 kHz.

14. The system of claim 12 wherein the voltage is about 10 to 500 volts rms.

15. The system of claim 12 wherein the probe further comprises an array of electrically isolated electrode terminals.

16. The system of claim 12 further comprising a return electrode positioned on the shaft of the probe proximal to the electrode terminal.

17. The system of claim 15 further comprising a plurality of power limiting elements each coupled between one of the electrode terminals and the power supply, wherein the power limiting elements independently limit power applied to the electrode terminals based on impedance between the electrode terminals and a return electrode.

18. The system of claim 12 further comprising a source of electrically conducting fluid for delivering electrically conducting fluid to the target site.

19. The system of claim 18 wherein the electrically conducting fluid is isotonic saline.

20. The system of claim 1 wherein the current limiting elements comprise a resonant circuit structure.

21. The system of claim 20 further comprising a return electrode, wherein the resonant circuit structure comprises a capacitor in series with each electrode terminal, and an inductor between each electrode terminal and the return electrode.

22. The system of claim 1 wherein the current limiting elements comprise inductors in series with each of the electrode terminals.

23. The system of claim 1 wherein the current limiting elements comprise capacitors in series with each of the electrode terminals.

24. An electrosurgical system for applying high frequency electrical energy to a tissue structure within or on a patient's body comprising:
    an electrosurgical probe comprising a shaft with a proximal end, a distal end and at least one electrode terminal at or near the distal end;
    a return electrode;
    an electrosurgical power supply coupled to the electrode terminal and the return electrode; and
    means for applying a high frequency voltage difference between the electrode terminal and the return electrode in the presence of electrically conductive fluid such that electric current flows from the electrode terminal, through the electrically conductive fluid, to the return electrode.

25. The system of claim 24 wherein the electrode terminal comprises a single electrode disposed near the distal end of an instrument shaft.

26. The system of claim 24 wherein the electrode terminal includes an array of electrically isolated electrode terminals disposed near the distal end of an instrument shaft.

27. The system of claim 24 wherein the electrically conductive fluid is selected from the group consisting essentially of blood and electrolytic irrigants.

28. The system of claim 24 wherein the return electrode is spaced from the electrode terminal such that when the electrode terminal is brought adjacent a tissue structure immersed in electrically conductive fluid, the return electrode is spaced from the tissue structure and the electrically conductive fluid completes a conduction path between the electrode terminal and the return electrode.

29. The system of claim 24 further comprising an electrically insulating support at the distal tip of the probe, the electrode terminal being substantially surrounded by the insulating support, the insulating support comprising an inorganic material.

30. The system of claim 29 wherein the inorganic material is selected from the group consisting essentially of ceramic, glass and glass/ceramic compositions.

31. The system of claim 24 wherein the power supply has an operating frequency of less than 400 kHz.

32. The system of claim 24 wherein the power supply has an operating frequency of about 100 kHz.

* * * * *